United States Patent [19]

Vanderlinde et al.

[11] Patent Number: 5,252,770

[45] Date of Patent: Oct. 12, 1993

[54] PROCESS FOR THE PRODUCTION OF CARBONATE ESTERS

[75] Inventors: William Vanderlinde, Creve Coeur; Donald E. Morris, Kirkwood, both of Mo.

[73] Assignee: Monsanto Company, St. Louis, Mo.

[21] Appl. No.: 361,158

[22] Filed: Jun. 5, 1989

[51] Int. Cl.$^5$ .............................................. C07C 69/96
[52] U.S. Cl. ................................................. 558/271
[58] Field of Search ........................................ 558/271

[56] References Cited

U.S. PATENT DOCUMENTS

| | | | |
|---|---|---|---|
| 2,837,555 | 6/1958 | Lee | 260/463 |
| 3,017,424 | 1/1962 | Meyer et al. | 260/463 |
| 3,030,335 | 4/1962 | Goldberg | 260/47 |
| 3,240,796 | 3/1966 | Thoma et al. | 260/453 |
| 3,256,198 | 6/1966 | Matzner | 252/99 |
| 3,272,750 | 9/1966 | Chase | 252/99 |
| 3,275,674 | 9/1966 | Bottenbruch et al. | 260/463 |
| 4,681,592 | 7/1987 | Hardy et al. | 8/111 |
| 5,075,476 | 12/1991 | Takeda et al. | 558/271 |
| 5,159,088 | 10/1992 | Schwalm | 558/271 |
| 5,183,918 | 2/1993 | Jakse et al. | 558/271 |
| 5,187,311 | 2/1993 | Takeda et al. | 558/271 |

FOREIGN PATENT DOCUMENTS

| | | | |
|---|---|---|---|
| 84677 | 8/1983 | European Pat. Off. | 558/271 |
| 0202698 | 11/1986 | European Pat. Off. | |
| 1128217 | 9/1968 | United Kingdom | 558/271 |

Primary Examiner—José G. Dees
Assistant Examiner—Dwayne C. Jones
Attorney, Agent, or Firm—R. C. Loyer

[57] ABSTRACT

The invention relates to a process of producing carbonate esters wherein an alkyl chloroformate is reacted with a phenolsulfonate in an alkaline medium and discloses the improvement of conducting the reaction in the presence of an organic solvent.

14 Claims, No Drawings

PROCESS FOR THE PRODUCTION OF CARBONATE ESTERS

BACKGROUND OF THE INVENTION

The present invention relates to the production of unsymetrical alkyl sulfophenyl carbonate esters wherein the carbonate ester product contains low levels of dialkylcarbonate impurities.

The ability of certain materials to bleach is widely known and consequently these materials can be used to remove discolorations or stains from articles. Although the exact mechanism by which bleaching agents function is only partially understood, it is generally known that many stains and soils possess a series of alternating single and double bonds and that loss of color can occur if one of the double bonds is destroyed. Thus, a material which can eliminate a double bond may be an effective bleach.

Categories of bleaches which are well known in the art include chlorine releasing components, inorganic oxygen bleaches and organic oxygen bleaches. Chlorine releasing compounds have certain disadvantages associated with their use such as, for example, their tendency to weaken or degrade fabrics, their tendency to react with other components of compositions in which they are present, their tendency to fade the colors of many dyed fabrics and to cause yellowing of certain synthetic or resin treated fabrics.

While inorganic oxygen bleaches overcome many of the disadvantages found with active chlorine releasing compounds, they have the disadvantage that they generally must be used at relatively high temperatures such as 85° C. or higher. This drawback becomes significant in light of the modern trend towards using lower wash temperatures, which are generally less than about 60° C., in order to reduce energy cost and prolong the life of the fabric. However, it is possible to improve the low temperature performance of inorganic oxygen releasing compounds through the addition of agents known as bleach activators. Generally, bleach activators react, in situ, with an inorganic oxygen bleach to generate a more reactive oxygen bleach such as peroxycarboxylic acid.

An example of prior art teaching of alkylsulfophenyl carbonate esters is European Patent Application 202,698 to Nollet, et al.

Consequently, there is a continuing need for an improved process for producing effective and skin-safe alkyl sulfophenyl carbonate.

SUMMARY OF THE INVENTION

Among those compounds which can be used as bleach activators are alkyl sulfophenyl carbonate esters. However, the prior art processes for production of this class of bleach activators yields products which have several significant disadvantages, for use as commercial bleach activators. Typically, these alkyl sulfophenyl carbonate esters have been synthesized in aqueous alkaline media via the reaction of alkyl chloroformate with the sodium salt of phenolsulfonic acid. However, because of the high alkalinity of the reaction medium to synthesize alkyl sulfophenyl carbonate esters, a certain portion of the desired product will decompose to yield dialkylcarbonates. As a consequence of the conversion of the alkyl sulfophenyl carbonate esters to dialkylcarbonates there is a decrease in bleach activator performance as well as cloudiness in aqueous solutions of the product (because of the poor water solubility of the dialkylcarbonate impurities).

More importantly, the dialkylcarbonates have been observed to be skin sensitizers as indicated by tests employing guinea pigs. Also, the presence of dialkylcarbonates as impurities in the sulfophenyl carbonate esters above certain levels make these impure esters potential skin sensitizers. In fact, alkylsulfophenyl carbonate esters produced by means of prior art processes have been observed as skin sensitizers in guinea pig tests at challenge levels of five percent or higher.

In accordance with the present invention there is provided an improved process for synthesizing alkyl sulfophenyl carbonate esters by reacting an alkyl chloroformate with a salt of phenolsulfonic acid in an alkaline medium, wherein levels of dialkyl carbonate impurities are reduced to such a low level that the product is skin-safe.

This invention relates to a process for synthesizing an alkyl sulfophenyl carbonate having a straight or branched chain alkyl group containing from about 6 to 12 carbon atoms or a cycloalkyl group containing about 6 to 9 carbon atoms wherein an alkyl haloformate is reacted with an alkali metal phenolsulfonate salt in an aqueous alkaline medium and contemplates the improvement comprising adding to the alkaline medium an organic solvent whereby the alkylsulfophenyl carbonate ester product is dissolved in the organic phase and thus separated from the alkaline medium.

The process of this invention allows the synthesis of alkyl sulfophenyl carbonate esters in an aqueous alkaline media environment but decreases the amount of alkyl sulfophenyl carbonate ester product which decomposes with time to yield dialkylcarbonate impurities. In so doing, alkylsulfophenyl carbonate ester product produced by the process of this invention contains lower levels of dialkylcarbonate impurities, especially as compared to such carbonate esters produced by precipitation from an aqueous alkaline reaction medium in the absence of an organic solvent.

The product made by the process of the invention retains more of its bleach activator activity, has a substantially reduced tendency to cause cloudiness in aqueous solutions and, finally, has a reduced tendency for skin sensitization.

DETAILED DESCRIPTION OF THE INVENTION

Prior art processes for production of carbonate esters have done so by reacting an alkyl, chloroformate and, preferably, sodium phenosulfonate salt in aqueous alkaline media. Unfortunately, because of the alkaline media a certain percentage of the alkylsulfophenyl carbonate esters which are formed in this manner decompose to yield dialkyl-carbonates which can cause skin sensitization and impart cloudiness to aqueous solutions of such products.

The peroxygen bleach activator compounds to which the process of this invention is directed are represented by the formula:

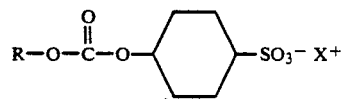

wherein R is a straight or branch chained alkyl group having from about 6 to about 12 carbon atoms and cycloalkyl groups having from about 6 to about 9 carbon atoms and X is a non-interfering cation such as sodium and mixtures thereof. These compounds are employed in combination with an inorganic peroxygen bleaching compound capable of yielding hydrogen peroxide in an aqueous solution to provide effective and safe fabric bleaching over a wide range of temperatures and conditions.

Preferably the alkyl group R in the above structural formula will contain from about 8 to about 10 carbon atoms while linear $C_9$ derivatives have been found to be most preferred. Compositions of this invention may comprise mixtures of compounds described by the above structural formula Such mixtures may contain compounds wherein R is $C_7$, $C_9$ and $C_{11}$ alkyl groups. Also, mixtures of compounds may be employed wherein R is $C_7$ and $C_9$ or preferably $C_8$ and $C_{10}$ alkyl groups. For example, compositions containing mixtures of compounds described by the above formula may contain, by weight, equal parts of compounds wherein R is $C_7$, $C_9$ and $C_{11}$ or the average carbon chain length present in the mixture may be adjusted by varying the amounts of and carbon chain lengths of the various compounds employed. A preferred mixture is one containing from 30/70 to 70/30 ratio by weight percent of $C_8$ and $C_{10}$ alkyl sulfophenyl carbonates.

The R groups of the above formula may contain substituents which are non-interfering with the bleach activator function of the compounds. Examples of non-interfering substituents are halides such as chlorine, bromine or iodine, nitro, cyano, sulfo, alkoxy, amino, carboxymethyl, etc.

The term "cation" employed hereinabove with respect to X in the structural formula refers to any non-interfering cation. By non-interfering it is meant that the cation will not interfere with the operation of the activator in producing a functional bleach or interfere with detergent action of a detergent material if present.

The most frequently employed cations are those of Group I of the Periodic Table, preferably sodium but encompassing also lithium and potassium, cesium and rubidium. Alkaline earth metal cations can also be employed as, for example, magnesium, calcium, strontium and barium, but in detergent applications the addition of calcium cations is not regarded as optimum. Ammonium and organic ammonium cations which can be prepared from low molecular weight organic amines, especially those having a molecular weight below about 300, are also considered non-interfering cations. Many other cations which do not interfere with the formation of bleach and its action in situ as well as other functions which may be desirable in conjunction with bleaching can also be employed such as sulfonium and sulfoxide cations.

The alkylsulfophenyl carbonate esters are prepared by reacting an alkyl haloformate with a salt of phenol sulfonate in an alkaline aqueous medium. In such a reaction the alkyl group of the haloformate corresponds to the desired R group of the formula set out earlier for the alkylsulfophenyl carbonate esters. Alkyl chloroformates are normally employed for the reaction and are preferred.

The reaction occurs in an alkaline aqueous medium generally at a pH of from about 10 to about 12 and at a temperature of from about 50° C. to about 100° C. The concentration of reactant and the duration of the reaction are easily within the skill of the art. Processes for the production of alkyl sulfophenyl carbonate esters are disclosed in European Patent Application 202,698 which is incorporated herein by reference.

According to this invention, the reaction is carried out in water and in the presence of an organic solvent, preferably a water-miscible organic solvent. Suitable solvents include methyl ethyl ketone, diethylketone, dimethyl ketone, dipropyl ketone, ethyl propyl ketone, and methyl propylketone.

The organic solvent is added in an amount sufficient to hold the product alkyl sulfophenyl carbonate in solution. Generally an amount equal to from 1-2 times by weight, of the expected product is added to the reactions mixture. More typically the organic solvent is added in an amount equal to about 1.5 times the weight of such expected product.

In the process of the invention the organic solvent can actually be present in the aqueous alkaline media at initiation of synthesis, or can be added during the reaction. When employing a water miscible organic solvent, phase separation begins to occur only after the by-product salt is produced. During reaction the alkylsulfophenyl carbonate product dissolves in the separate organic phase thereby separating such product from the highly alkaline environment likely to cause degradation and resultant formation of dialkylcarbonate. Alkylsulfophenyl carbonate ester is separated and may then be washed one or more times. Washing can be accomplished with, for example, a 30% sodium sulfate aqueous solution. The alkylsulfophenyl carbonate ester product can then be isolated by stripping off the organic solvent and evaporating off the residual water.

The process of the present invention provides product having significantly lower levels of dialkylcarbonate impurities over prior art techniques in which the alkylsulfophenyl carbonate esters are synthesized and precipitated from an aqueous alkaline reaction medium alone.

In a preferred embodiment of this invention the separated organic layer is washed with a suitable neutral salt such as an alkali metal sulfate. Extremely low levels of dialkylcarbonate in the alkyl sulfophenyl carbonate results by such washing which is accomplished by simple mixing of a aqueous solution of the salt with the organic phase from the reaction product. Multiple washings, such as 2 or 3 repeated washings, has provided alkyl sulfophenyl carbonates produced in accordance with this invention having very low levels of dialkylcarbonate. Typically, the organic layer is washed with an aqueous solution of neutral salt having a concentration of from about 20% to about 40%, by weight, and more usually with an aqueous solution having a concentration of from about 30% to about 35%, by weight. Preferred neutral salts include sodium sulfate, trisodium phosphate and sodium nitrate.

The organic layer is recovered from the washing step by separation means similar to those employed to recover the organic layer from the reaction mixture.

The above disclosure generally describes the present invention. A more complete understanding can be obtained by reference to the following specific examples which are provided herein for the purposes of illustration only and are not intended to limit the scope of the invention. Unless otherwise stated, all references to percent is percent by weight in the following examples.

EXAMPLE 1

Prior Art

A reactor having a capacity of 378 liters was purged with nitrogen and then protected with nitrogen while being charged with 86.2 kg of water. With agitation 31.6 kg of sodium 4-phenolsulfonate were added. After 10 minutes of agitation 12.8 kg of 50% sodium hydroxide was added over a period of 15 minutes. To serve as an emulsifying agent, 90.7 g of product was added. The batch was heated to 50° C. and a 50/50, by weight, mixture of n-octyl-chloroformate and n-decyl chloroformate were added, 32.1 kg, over a 15 minute period. The batch heated to 65° C. following addition of the chloroformate and was held at a temperature in the range of from 60° C.–70° C. for 30 minutes. The reaction mixture was diluted with 99.9 kg of water and cooled to a temperature of from 0–5° C. The product was filtered after a 1-hour holding period by means of a centrifuge and spun dry. After pan drying at 50° C. with vacuum about 45.4 kg of a 50/50, by weight, mixture of n-octyl sulfophenyl carbonate and n-decyl sulfophenyl carbonate was obtained.

The product was found to contain 4.63 percent, by weight, of mixed dialkylcarbonates (n-octyl/n-decyl) by analysis of a cyclohexane extract.

EXAMPLE 2

Into a reactor as described in Example 1 and with similar procedure were charged 40.9 kg of water and, with agitation, 24.9 kg of sodium 4-phenolsulfonate. The mixture was stirred for 10 minutes and then 9.72 kg of 50 percent sodium hydroxide were added over a period of 15 minutes. There were then added 9.72 g of product and 68.18 kg of methyl ethyl ketone. After heating the reaction mixture to 50° C., there was added 24.5 kg of 50/50 mixture, by weight, of n-octyl chloroformate and n-decyl chloroformate over a period of 15 minutes. The reaction was carried out at a temperature in the range of from 65° C. to 70° C. for a period of 30 minutes. Afterward the reaction mass was cooled to below 50° C. and agitation stopped to allow the mixture to settle. Two liquid phases formed.

The organic layer, containing the desired mixture of alkyl sulfophenyl carbonate and was separated from, the aqueous layer. The organic phase was then pan dried with vacuum to provide about 45.45 kg of a 50/50 mixture, by weight, of n-octyl/n-decyl sulfophenyl carbonate. Analysis (gc) of a cyclohexane extract of the product indicated that it contained 1.67 percent of a mixture of the dialkylcarbonates comprising the n-octyl and n-decyl species. The above level of concentration of dialkylcarbonate in alkyl sulphenyl carbonate has been shown not to be a skin sensitizer in tests.

EXAMPLE 3

Into a reactor as described in Example 1 and with similar procedure there were charged 40.9 kg of water and, with agitation, 24.5 kg of sodium 4-phenolsulfonate. After an additional 10 minutes of agitation, there was added 9.7 kg of 50%, by weight, sodium hydroxide over a period of 15 minutes. There were then added 9.72 g of product and 68.1 kg of methylethyl ketone. After heating the mixture to 50° C. there was added 19.5 kg of n-hexylchloroformate over a period of 15 minutes. During addition of the chloroformate the batch temperature increased to about 65° C. and the reaction allowed to proceed with agitation for a period of 30 minutes at a temperature in the range of 65° C.-70° C. After completion of the reaction the mixture was cooled to below 50° C. and allowed to settle into two phases. The top organic layer containing n-hexylsulfophenyl carbonate was separated from the bottom saturated layer, and was washed with 22.72 kg of a 33 percent aqueous solution of sodium sulfate. After thorough mixing the mixture was allowed to settle. The top organic layer was separated from the bottom salt layer and the procedure with sodium sulfate repeated two more times. The organic layer was pan dried with vacuum. About 45.4 kg of n-hexyl sulfophenyl carbonate was obtained which contained 0.92 percent di-n-hexyl carbonate as indicated by analysis (gc) of a cyclohexane extract.

EXAMPLE 4

Delayed contact hypersensitivity studies (Buehler Assay) were conducted employing an aqueous solution of a 50/50, by weight, mixture of n-octyl n-decyl sulfophenyl carbonate product of Example 1. In this test Hartely albino guinea pigs were divided into four groups consisting of 4 males and 4 females (group 1), 10 males and 10 females (group 2). Group 1 was used to determine the appropriate concentrations of test material for use during the study phases. The animals of group 2 were treated at induction with a 5 percent concentration of the test material and later challenged with a 2.5 percent concentration of the test material. Rechallenge concentrations were 2.5 percent and 1 percent. Groups 3 and 4 were treated only during the challenge and rechallenge phases respectively, to act as irritation controls. The sample tested was applied in patches on test sites once a week for three weeks (3 exposures). After a two week rest period, animals were treated at new sites with the challenge concentrations noted above. Rechallenges were carried out one week after the primary challenge. Scores of 1 or greater in the test group are indicative of sensitization provided scores of less than 1 were present in the irritation control groups (groups 3 and 4). If grades of 1 or greater are found in the irritation control group, then the test group must have reactions exceeding those of the control group to be considered sensitized. The test sample of the 50/50 mixture of n-octyl sulfophenyl carbonate and n-decyl sulfophenyl caused slight patchy erythema in one animal after the second induction and in 10 animals after the third induction. After the first challenge one animal had a score of 1 at both 24 and 48 hours, while 9 animals at 24 hours and 10 animals at 48 hours had scores of±(slight patchy erythema). The rechallenge at 2.5 percent concentration produced a score of 1 in one animal and a score of±at 48 hours in 9 animals. Rechallenge at 1 percent produced slight patchy erythemia in two animals at 48 hours. None of the irritation control animals responded to either concentration of the sample material. The results indicate that sensitization occurred at 2.5 percent challenge and rechallenge while the slight response at 1 percent concentration is equivocal.

EXAMPLE 5

A delayed contact hypersensitivity study as described in Example 4 was repeated by employing samples of alkyl sulfophenyl carbonates. The first sample was the product produced in accordance with the procedure of Example 1 which was purified by extraction with cyclohexane to remove dialkylcarbonates. The second sample was the purified product of Example 1 to which was added 4.63 percent, by weight, of a 50/50 mixture of di-n-octyl and di-n-decyl carbonates. The concentration of the challenge solution was 10 percent, by weight, of total carbonate. On the basis of a screen for primary irritation an induction solution of the product at a 10%, by weight, concentration was employed. During induction the test material was applied on patches to the same site once a week for three weeks. Two weeks after the last induction, the guinea pigs were challenged at new sites with two materials. Scores of 1 or greater indicated sensitization in the absence of a similar response in control animals. In this test, the purified sample, having the dialkylcarbonate removed, produced no scores of 1 or greater in the test group. When the dialkylcarbonates were added to the purified sample, scores of 1 in two of 20 animals were observed while none of the controls responded. The results indicate that the dialkylcarbonates were responsible for the sensitization response produced by the contaminated product.

EXAMPLE 6

2-Ethylhexyl sulfophenyl carbonate was prepared combining in a suitable reaction vessel 10.9 g of disodium phenosulphonate (0.05 moles) and 9.6 g of 2-ethylhexyl chloroformate (0.05 mole) at a pH of about 10 in the presence 30 g of methyl ethyl ketone. The mixture was heated in an oil bath at 70° C. for 30 minutes with agitation.

Phase segregation occured and after the reaction, the organic phase containing the alkyl sulfophenyl carbonate was separated and washed with a 30% sodium sulfate aqueous solution. The product was isolated from the aqueous solution by stripping off the methyl ethyl ketone and by evaporating off the water.

The resulting product was non-cloudy in water solutions upon redissolving and was not a skin sensitizer at 5% levels of challenge.

EXAMPLE 7

In the manner of Example 6 n-decyl sulfophenyl carbonate was prepared from n-decyl chloroformate and sodium phenolsulfonate. After separation and washing, the product was found to be n-decyl sulfophenyl carbonate. The product was found to have a yield of 94% active material.

We claim:

1. In a process for synthesizing a non-skin sensitizing sulfophenyl alkyl carbonate having a straight or branched chain alkyl group containing from about 6 to about 12 carbon atoms or a cycloalkyl group containing from about 6 to about 9 carbon atoms wherein an alkyl chloroformate is reacted with a phenolsulfonate in an aqueous alkaline medium, the improvement which comprises adding to said alkaline medium a water-miscible organic solvent whereby a separate organic phase is formed after the initiation of said reaction and whereby the sulfophenyl alkyl carbonate product is removed from said alkaline medium and enters into the organic phase upon its formation thereby avoiding formation of skin sensitizing amounts of dialkylcarbonate.

2. The process of claim 1, wherein said organic solvent is added to said alkaline reaction medium after initiation of said synthesis.

3. The process of claim 1, wherein said organic solvent is present in said alkaline reaction medium at initiation of said synthesis.

4. The process of claim 1, wherein said water miscible solvent is methyl ethyl ketone.

5. The process of claim 4, wherein the alkyl chloroformate is a mixture of two or three different alkyl chloroformates.

6. The process of claim 5, wherein the alkyl group contains from 8 to 11 carbon atoms.

7. The process of claim 6, wherein the alkyl chloroformate is a mixture comprising octyl and decyl chloroformate.

8. The process of claim 7, wherein the mixture comprises from about 30 to 70 percent, by weight, of octyl chloroformate and from about 70 to 30 percent, by weight, decyl chloroformate.

9. The process of claim 1, wherein the phenolsulfonate is an alkali metal phenolsulfonate.

10. The process of claim 1, wherein organic solvent is present in an amount equal to about 1.2 to about 2 times, by weight, of the alkyl sulfophenyl carbonate.

11. The process of claim 1, wherein the alkyl chloroformate is octyl chloroformate.

12. The process of claim 1, wherein the alkyl chloroformate is n-decyl chloroformate.

13. The process of claim 1, wherein the alkyl chloroformate is n-hexyl chloroformate.

14. The process of claim 1, wherein the alkyl chloroformate is 2-ethyl-hexyl chloroformate.

* * * * *